United States Patent [19]

Erichsen et al.

[11] 4,381,768

[45] May 3, 1983

[54] KNEE ORTHOSIS

[75] Inventors: Charles W. Erichsen, Covina; Michael A. Bleemers, San Dimas, both of Calif.

[73] Assignee: Stainless Mfg., Inc., San Dimas, Calif.

[21] Appl. No.: 264,689

[22] Filed: May 18, 1981

[51] Int. Cl.³ .............................................. A61F 3/00
[52] U.S. Cl. ................................................. 128/80 C
[58] Field of Search ................ 128/80 C, 80 F, 80 R, 128/87 R, 88

[56] References Cited

U.S. PATENT DOCUMENTS

| | | |
|---|---|---|
| 1,622,211 | 3/1927 | Sheehan ........................ 128/80 C X |
| 2,532,955 | 12/1950 | Shook . |
| 3,350,719 | 11/1967 | McClure, Jr. . |
| 3,387,305 | 6/1968 | Shafer . |
| 3,581,741 | 6/1971 | Rosman et al. .................... 128/80 C |
| 3,669,105 | 6/1972 | Castiglia ............................ 128/80 C |
| 3,779,654 | 12/1973 | Horne . |
| 3,786,804 | 1/1974 | Lewis . |
| 3,885,252 | 5/1975 | Nakajima . |
| 3,898,697 | 8/1975 | Whitehead . |
| 3,934,583 | 1/1976 | Hollingshead et al. . |
| 3,945,046 | 3/1976 | Stromgren . |
| 4,183,099 | 1/1980 | Lacey . |

FOREIGN PATENT DOCUMENTS 528240 6/1955 Italy .................................. 128/80 F Primary Examiner—John D. Yasko
Attorney, Agent, or Firm—William W. Haefliger

[57] ABSTRACT

A knee orthosis incorporates first and second elongated rigid members attachable to the sides of upper and lower leg extents; together with means pivotally coupling the members proximate the knee location, and inter-meshed gear parts respectively carried by the members to relatively rotate as either of the rigid members pivots. Multiple adjustable attachment straps are also provided, two of the straps extending in criss-cross relations behind the knee.

7 Claims, 6 Drawing Figures

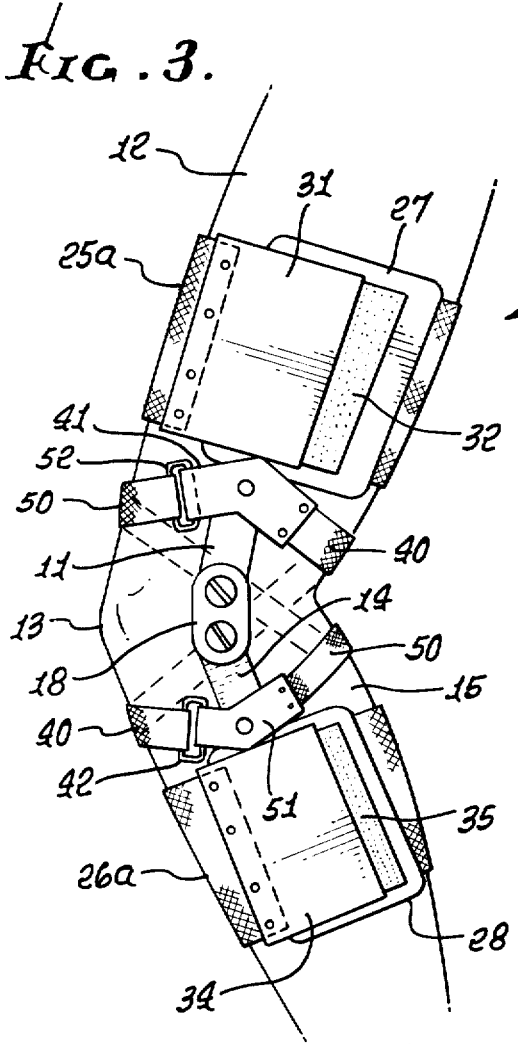
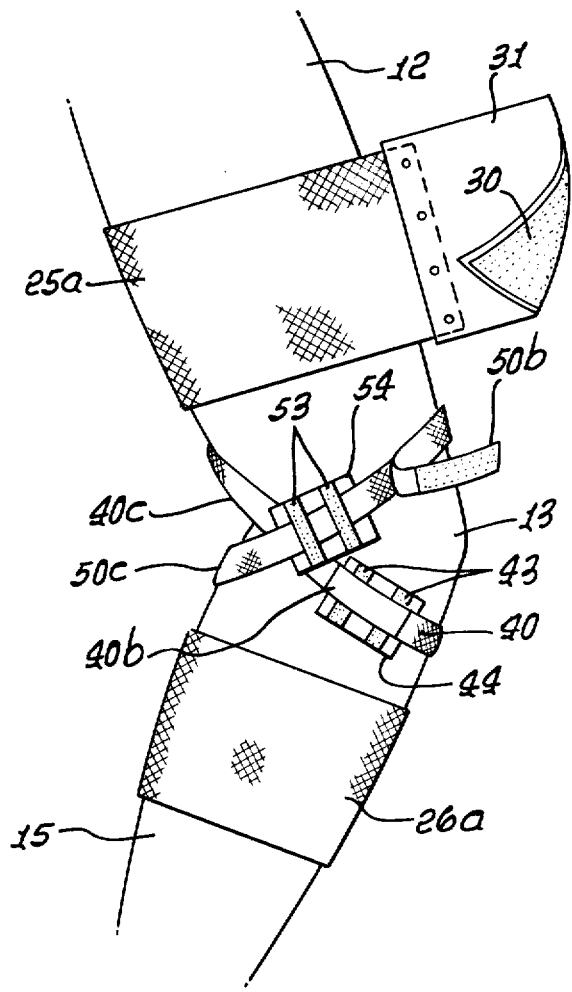
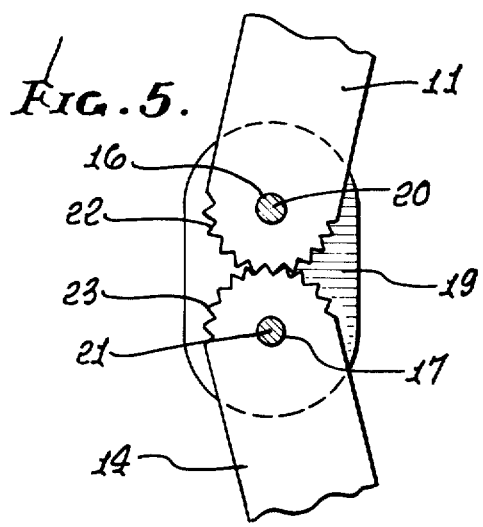
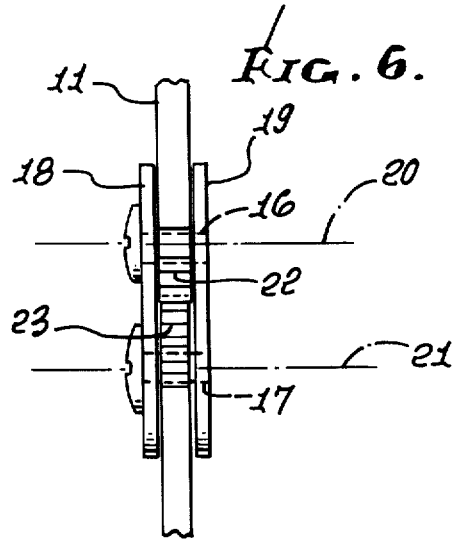

KNEE ORTHOSIS

BACKGROUND OF THE INVENTION

This invention relates generally to human limb bracing techniques, and more particularly concerns an athletic knee orthosis having uncommonly favorable characteristics.

The field of sports medicine has evolved in the past few years from a fledgling with basically no following into a growing, viable, integral part of orthopaedic surgery. In the past, little thought went into mechanism of injury, post injury rehabilitation, and return to active sports participation.

Within the last few years, major advances have been made in all of the above, including bracing techniques. For years the standard of post knee injury was an elastic knee cage. This evolved into the so-called Lennox-Hill brace and its modifications. While that brace was effective; because of its bulky nature it has not met the needs of many professional as well as "weekend" athletes. Also the Lennox-Hill type braces could not be worn with the type of garment necessary for this sports activity, and typically were left in the back seat of the car when the participant returned to his racing activity.

SUMMARY OF THE INVENTION

It is a major object of the invention to provide an orthosis that overcomes the disadvantages and difficulties of prior braces, and which affords unusual advantages of its own. Basically, the device comprises:

(a) a first elongated rigid member attachable to the side of the upper leg while extending generally in the direction thereof, (b) a second elongated rigid member attachable to the side of the lower leg while extending generally in the direction thereof, (c) means pivotably coupling the members, proximate the knee location, and (d) intermeshed gear parts respectively carried by the members to relatively rotate as either of the members pivots relative to the other of said members.

These and other objects and advantages of the invention, as well as the details of an illustrative embodiment, will be more fully understood from the following description and drawings, in which:

DRAWING DESCRIPTION

FIG. 3 is a frontal view like FIG. 1, but showing the device applied to the leg of a user;

FIG. 4 is a rear elevation of the device as seen in FIG. 3;

FIG. 5 is an elevation showing gearing interconnecting orthosis device members; and FIG. 6 is a view taken on lines 6—6 of FIG. 1.

DETAILED DESCRIPTION

Figure 1:
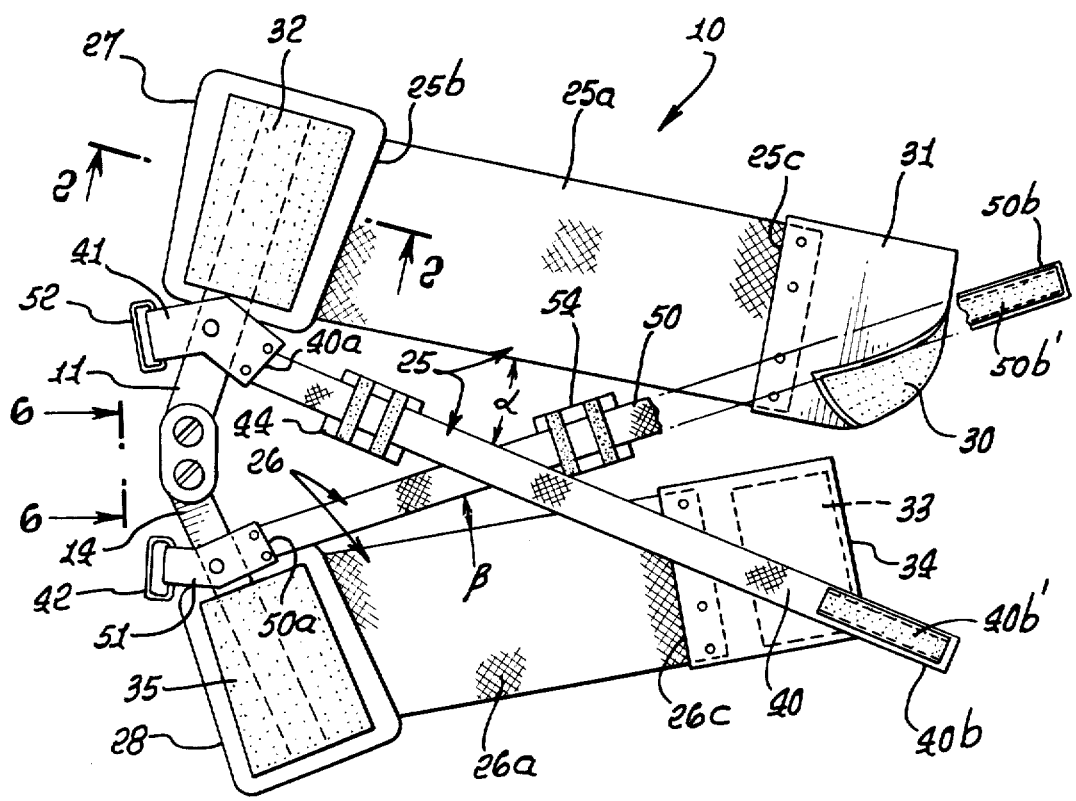
FIG. 1 is a side elevation showing the orthosis device in extended condition.

The illustrated device 10 includes a first elongated member such as lightweight metal bar or link 11 attachable to the outer side (see FIG. 3) of the upper leg 12 of the user, to extend in the direction of that upper leg (i.e. thigh) above the knee 13. The device 10 also includes a second elongated member such as lightweight metal bar or link 14 attachable to the outer side (see FIG. 3) of the lower leg (i.e. calf) 15 of the user, to extend in the direction of that lower leg, below the knee. Members 11 and 15 may consist of aluminum for example.

Also provided is means pivotally coupling the members, proximate the knee location, together with intermeshed gear parts respectively carried by the members to relatively rotate as either of the members pivots relative to the other of the members, thereby controlling such relative rotation. In the example, such means is shown to include two pivots at 16 and 17 having spaced, parallel axes 20 and 21 (which are horizontal if the members 11 and 14 extend in a vertical plane), the pivots connected by parallel links 18 and 19 as shown in FIG. 6. Thus, were it not for the gearing to be described, the members 11 and 14 could freely and independently pivot about pivot axes 20 and 21. The gearing is shown to include spur gear teeth 22 on the lower end of member 11 meshing with spur gear teeth 23 on the upper end of member 14, teeth 22 centered about axis 20, and teeth 23 centered about axis 21. As a result, member 11 can rotate clockwise about axis 20 only if member 14 rotates counterclockwise about axis 21, and vice versa; alternatively, member 14 can rotate counterclockwise about axis 21, in FIG. 3, only if links 18 and 19 swing counterclockwise about axis 20, with member 11 not rotated about axis 20, and vice versa, and member 11 can rotate counterclockwise about axis 21 only if links 18 and 19 swing counterclockwise about axis 21, with member 14 not rotated about axis 20, and vice versa. Combinations of these movements can also occur. Accordingly, good control, with stability, over leg movement is achieved, when member 11 is connected to upper leg 12, and member 14 is connected to lower leg 15.

Figure 2:
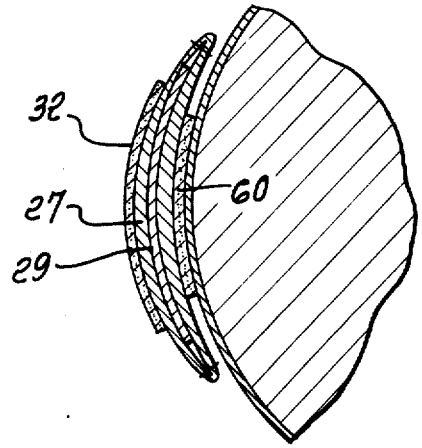
FIG. 2 is a section taken on lines 2—2 of FIG. 1.

Unusually advantageous means to attach the members 11 and 14 to the upper and lower leg elements will now be described. First strap means, as at 25 is carried by first member 11, and second strap means, as at 26, is carried by second member 14. The first means 25 includes a relatively wide first elastic strap 25a having an end 25b anchored as by pad 27 to first member 11, and opposite end 25c, and adapted to be wound tightly about the upper leg. The second strap means as at 26 includes a relatively wide second elastic strap 26a having an end anchored as by pad 28 to second member 14, and an opposite end 26c, and adapted to be wound tightly about the lower leg. Pads 27 and 28 are C-shaped or arcuate (see FIG. 2), so that their concave sides fit the wearer's upper and lower legs, as in FIG. 2. They may consist of leather, for example, and contain corresponding C-shaped metal inserts 29 integral with the members 11 and 14.

VELCRO connections are provided on the straps 25 and 26 to hold them in wound condition on the wearer's legs. Thus, VELCRO connection 30 on a leather end extension 31 of strap 25 is adapted to engage VELCRO connection 32 on pad 27; and VELCRO connection 33 on a leather end connection 34 or strap 26 is adapted to engage VELCRO connection 35 on pad 28. The members 11 and 14 are then tightly held to the user's upper and lower legs (see FIG. 3).

The first strap means may also, with unusual advantage include a relatively narrow non-elastic primary strap 40 having an end 40a anchored at 41 to the upper member 11, and so as to extend at an angle α relative to the first strap 25a (see FIG. 1); and having a free opposite end 40b, the strap adapted to be wound about the rear of the knee for connection to the lower member.

See for example in FIGS. 3 and 4 the extension of the strap 40 behind the knee at 40c, and then passage of the strap through metallic loop 42 attached to member 14, the strap free end 40b then turned back for connection to the strap 40 (see FIG. 4), as via VELCRO 40b' on free end 40b, and VELCRO 43 on a pad 44 slidable on and along strap 40.

Similarly, the second strap means may also, with unusual advantage, include a relatively narrow, non-elastic secondary strap 50 having an end 50a anchored at 51 to lower member 14, and so as to extend at an angle $\beta$ relative to the second strap 26a; and having a free opposite end 50b, the strap adapted to be wound about the rear of the knee (in criss-cross relation to strap 40) for connection to the upper member 11. See for example in FIGS. 3 and 4 the extension of the strap 50 behind the knee at 50c, and then passage to the strap through metallic loop 52 attached to member 11 via connection 41, the strap free end 50b then turned back for connection to the strap 50 as via VELCRO 50b' on free end 50b, and VELCRO 53 on a pad 54 slidable on and along strap 50. When straps 40 and 50 are thus tightened, the upper and lower members 11 and 14 are further interconnecting, for stability, and in a manner that causes the strap attachments to the members 11 and 14 via loops 42 and 52 to move apart, relatively, while the strap connection at 40a and 50a to the members 11 and 14 move relatively toward one another, during leg flexing, for stability.

The user way wear a pantleg such as a polyurethane sleeve over his calf, knee and thigh, and the brace adapts itself readily thereto. Thus, pads 27 and 28 may carry VELCRO 60 at their concave inner sides, to connect to such a sleeve.

We claim:
1. In a knee orthosis, the combination comprising
   (a) a first elongated rigid member attachable to the outer side of the upper leg while extending generally in the direction thereof,
   (b) a second elongated rigid member attachable to the outer side of the lower leg while extending generally in the direction thereof,
   (c) means pivotally coupling said members, proximate the knee location,
   (d) inter-meshed gear parts respectively carried by said members to relatively rotate as either of said members pivots relative to the other of said members,
   (e) first straps on and spaced along the first member and adapted to be wound about at least the upper leg, and second straps on and spaced along the second member and adapted to be wound about at least the lower leg, whereby the first and second members are held in position relative to the upper and lower legs with the gear parts located laterally proximate the knee location, and
   (f) pads on said members and shaped to fit against said upper and lower legs, at least two of said first and second straps associated with said pads to hold the pads in place,
   (g) said first straps including a relatively wide first strap having an end anchored to said first member and an opposite end adapted to wind about the upper leg, and said second straps including a relatively wide second strap having one end anchored to said second member and an opposite end adapted to wind about the lower leg,
   (h) said first straps including a relatively narrow primary strap having one end anchored to said upper member so as to extend at an angle to said wide first strap, and having a free opposite end adapted to wind about the rear of the knee for connection to the lower member,
   (i) said one end of the narrow primary strap anchored closer to said gear parts than said end of the wide first strap, said lower member having a connection thereon for receiving said free opposite end of the primary strap, said connection located closer to the gear parts than said end of the wide second strap,
   (j) said second straps including a relatively narrow secondary strap having one end anchored to said lower member so as to extend at an angle to said wide second strap, and having a free opposite end adapted to wind about the rear of the knee for connection to the upper member,
   (k) said one end of the narrow secondary strap anchored closer to said gear parts than said end of the wide second strap, said upper member having a connection thereon for receiving said free opposite end of the secondary strap, said connection located closer to said gear parts than said end of the wide primary strap,
   (l) whereby when said one ends of the primary and secondary straps move relatively toward one another as said gear parts relatively rotate, said opposite ends thereof move relatively apart.

2. The combination of claim 1 wherein said (c) means defines two pivots respectively associated with said members, said pivots having parallel axes, there being two of said gear parts having teeth located generally between said two axes.

3. The combination of claim 1 including VELCRO sliders on said primary and secondary straps and VELCRO connectors on the ends of said primary and secondary straps adapted to engage said sliders.

4. The combination of claim 1 including an expansible fabric sleeve extending over at least one of said members.

5. The combination of claim 1 wherein said (c) means also includes link means interconnecting said two pivots, said teeth of one part centered about one axis, and the teeth of the other part being centered about the other axis.

6. The combination of claim 1 including VELCRO on the pads at concave innersides thereof, to attach to clothing on the wearer's legs.

7. The combination of claim 1 including VELCRO connections on said first and second straps to hold them in wound condition, on said upper and lower legs respectively.

* * * * *